(12) United States Patent
Cabanis et al.

(10) Patent No.: US 7,305,898 B2
(45) Date of Patent: Dec. 11, 2007

(54) INSTALLATION FOR NON-DESTRUCTIVE INSPECTION OF A PART

(75) Inventors: Patrick Cabanis, Ozouer le Voulgis (FR); Richard Coulette, Gentilly (FR); Christian Marceau, Lieusaint (FR)

(73) Assignee: Snecma Moteurs, Paris (JP)

( * ) Notice: Subject to any disclaimer, the term of this patent is extended or adjusted under 35 U.S.C. 154(b) by 155 days.

(21) Appl. No.: 11/143,484

(22) Filed: Jun. 3, 2005

(65) Prior Publication Data
US 2005/0274188 A1     Dec. 15, 2005

(30) Foreign Application Priority Data
Jun. 11, 2004   (FR) .................................. 04 06340

(51) Int. Cl.
*G01M 19/00* (2006.01)
(52) U.S. Cl. .................................................. 73/865.8
(58) Field of Classification Search ............... 73/865.8, 73/635, 637, 639, 644, 622, 643, 625, 618–620
See application file for complete search history.

(56) References Cited

U.S. PATENT DOCUMENTS

| | | | |
|---|---|---|---|
| 4,817,016 A * | 3/1989 | Thompson et al. ........... 73/598 |
| 5,161,413 A * | 11/1992 | Junker et al. ................. 73/634 |
| 5,275,052 A * | 1/1994 | Luttrell et al. ............... 73/619 |
| 5,515,728 A * | 5/1996 | Casarcia et al. .............. 73/623 |
| 5,670,879 A | 9/1997 | Zombo et al. |
| 5,710,378 A | 1/1998 | Dykes et al. |
| 5,781,007 A | 7/1998 | Partika et al. |
| 6,487,922 B1 | 12/2002 | Bauer et al. |
| 6,792,809 B1 * | 9/2004 | Moore ......................... 73/618 |
| 7,093,491 B2 * | 8/2006 | Murphy et al. ............... 73/620 |

* cited by examiner

*Primary Examiner*—Hezron Williams
*Assistant Examiner*—Nashmiya Fayyaz
(74) *Attorney, Agent, or Firm*—Oblon, Spivak, McCelland, Maier & Neustadt, P.C.

(57) ABSTRACT

An installation for non-destructive inspection makes use simultaneously of sensors responsive to different physical characteristics. In an example, a sensor support, e.g. a kind of carriage having running wheels via which it comes into contact with the surface to be inspected, is fitted with two types of sensor, namely an eddy current sensor and at least one ultrasound sensor.

17 Claims, 3 Drawing Sheets

INSTALLATION FOR NON-DESTRUCTIVE INSPECTION OF A PART

The invention relates to an installation for non-destructive inspection of a part, and in particular a part of relatively large dimensions and complex shape, such as the rotor of a high pressure compressor, for example. The invention relates more particularly to an arrangement of sensors enabling a plurality of measurements to be performed simultaneously, thereby reducing the time required for acquiring the data needed to evaluate the state of the part.

BACKGROUND OF THE INVENTION

Certain parts of complex shape that are subjected to high levels of mechanical and thermal stress, such as a rotor of a high pressure compressor in a turbojet, for example, require rigorous inspection prior to being put into operation or during an overhaul. For example, such a rotor is made up of a plurality of spaced-apart titanium or nickel-based alloy disks that are welded together, and they therefore include annular cavities that have the reputation of being difficult to access. These cavities are the spaces between the disks. Various kinds of defect or damage can affect the rotor, and in particular its inside disks. For example, it is known that the titanium alloy from which they are made might contain inclusions. Such non-uniform regions create zones of weakness in the metal. By way of example, they can be detected by ultrasound examination. It is also possible that cracks will appear, in particular after operating for a certain length of time. Such defects may be detected, for example, by undertaking examination using an eddy current probe. Until now, it has not been envisaged to inspect the inside disks of such a part. The invention makes this operation possible.

OBJECTS AND SUMMARY OF THE INVENTION

More particularly, the invention relates to an installation for non-destructive inspection of a part having an axis of revolution and including annular cavities on a common axis and axially adjacent to one another, the installation comprising a sensor support suitable for moving over a surface of said part to be inspected, and means for combining circular displacement and radial displacement of said support and/or of said part, and said support being fitted with a plurality of sensors for sensing different physical characteristics in order to pick up data groups specific to said sensors, and corresponding to respective defined zones of said surface, in a single scan thereof.

The surface to be inspected is not completely flat: radially it is of varying dimensions.

In a presently preferred embodiment, said support is fitted with an eddy current sensor and with at least one ultrasound sensor. Preferably, said support is fitted with two ultrasound sensors disposed on either side of said eddy current sensor.

It is also possible to have a plurality of eddy current sensors with different characteristics, and more generally a plurality of sensors making use of different physical phenomena.

Advantageously, said sensor support includes running wheels via which it remains in contact with said surface to be inspected throughout a scan. In this way, the optimum distance between the sensors and the material under inspection is maintained continuously.

In addition, the support may be constrained to move in a coupling liquid that is necessary or at least advantageous when inspecting by means of ultrasound. Conventionally, the coupling liquid is water. For this purpose, the part to inspected can be fully immersed in a vessel filled with water, and the support moves in said vessel while remaining in contact with the part to be inspected.

For a support carrying an eddy current sensor together with two ultrasound sensors, the eddy current sensor is arranged in the support so as to be placed facing an individual zone that is being inspected of the part under inspection, while the two ultrasound sensors are installed on the support so that their action axes converge substantially towards said individual zone. For ultrasound inspection, it has been found advantageous to scan the surface to be inspected at a plurality of angles of incidence. For example, the axes may lie in a common plane. Furthermore, in order to ensure that the ultrasound sensors do not interfere with each other, they may be operated in alternation.

BRIEF DESCRIPTION OF THE DRAWINGS

The invention can be better understood and other advantages thereof appear better in the light of the following description of an installation for non-destructive inspection of a part, the installation being fitted with a set of sensors in accordance with the principles of the invention. The particular installation described is given by way of example, and the description is made with reference to the accompanying drawings, in which.

MORE DETAILED DESCRIPTION

Figure 1:
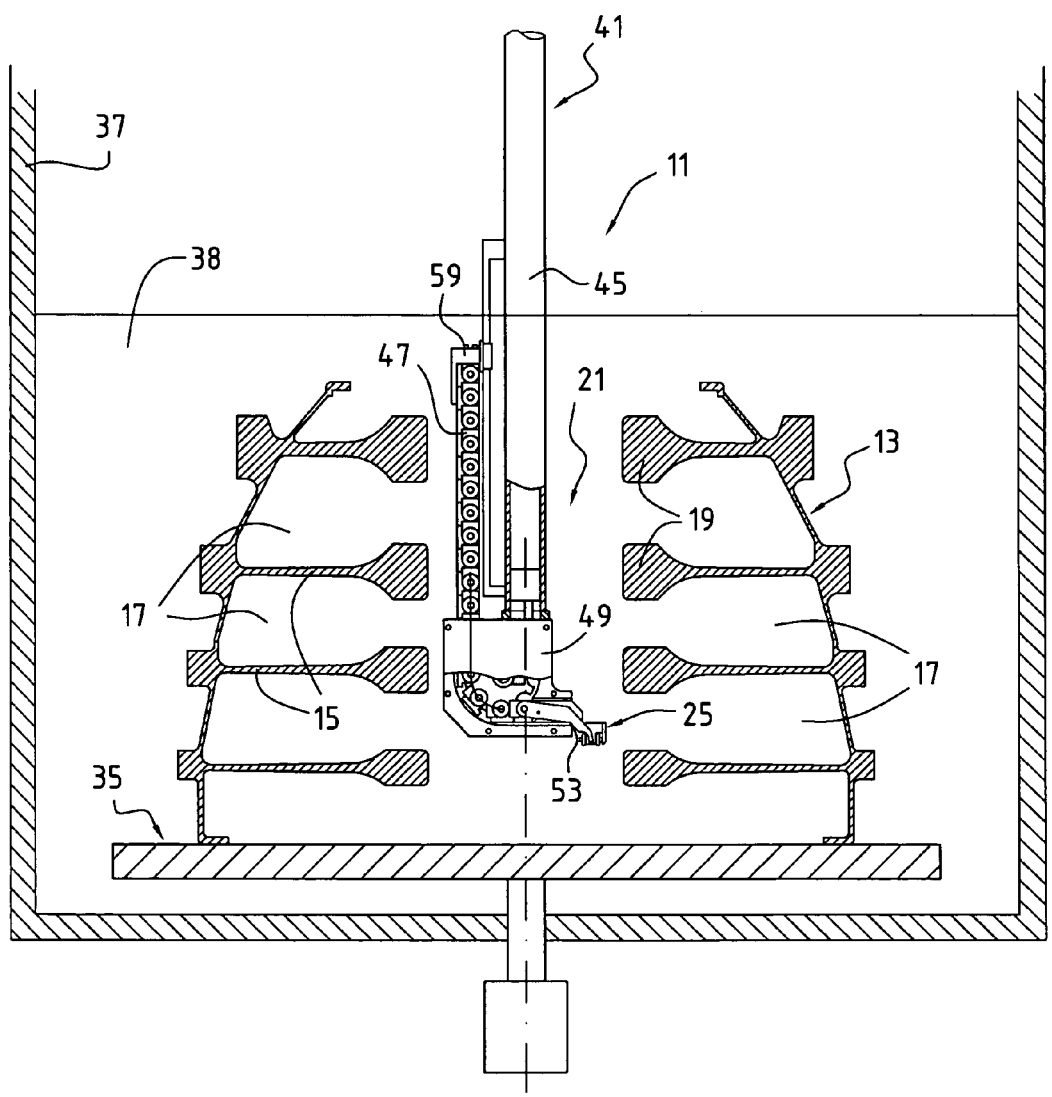
FIG. 1 is a diagrammatic view of an installation for non-destructive inspection of a rotor of a high pressure compressor.
Figure 2:
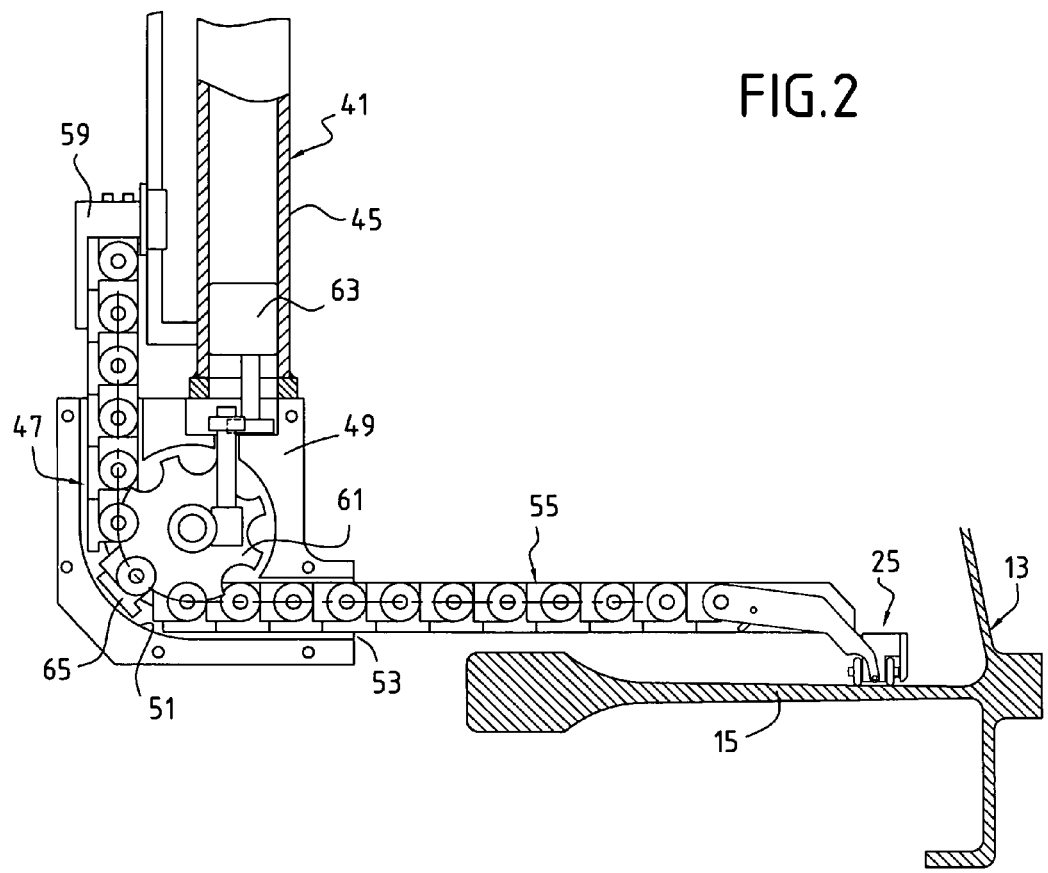
FIG. 2 is a detail view on a larger scale showing the installation and how the surface one of the disks of said rotor is scanned.
Figure 3:
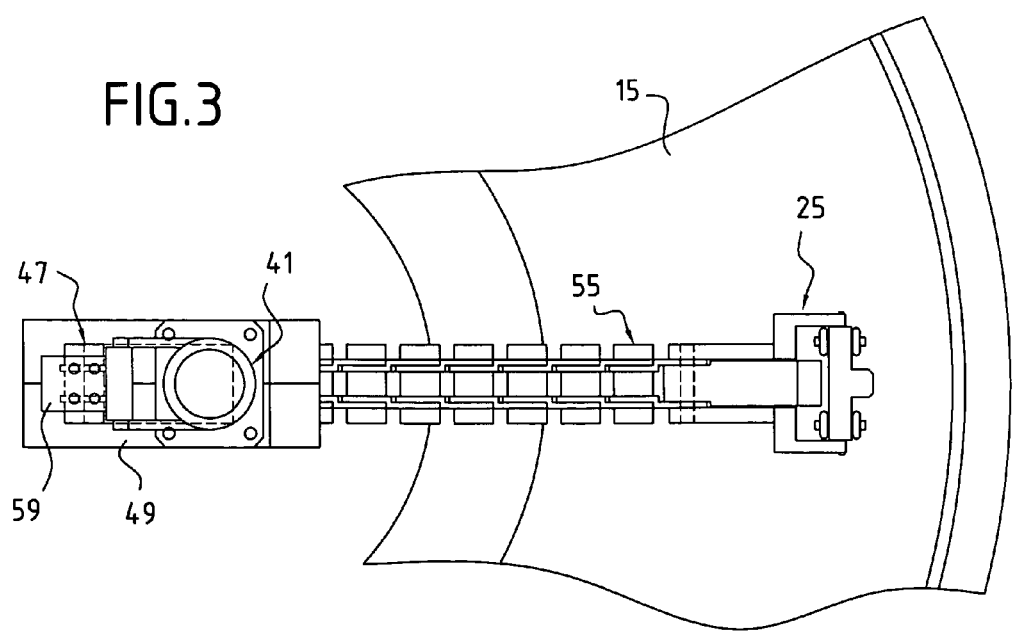
FIG. 3 is a plan view corresponding to FIG. 2.
Figure 5:
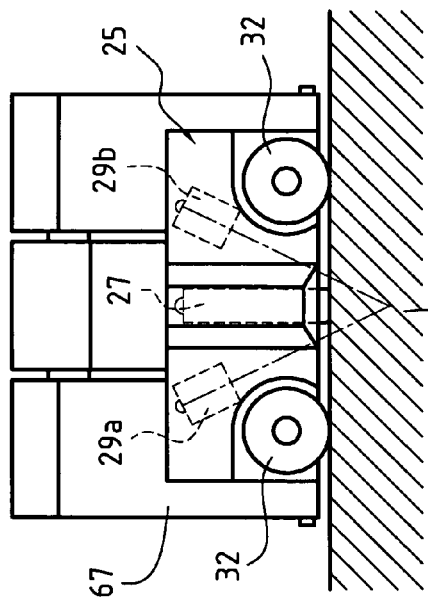
FIG. 5 is a view seen looking along V in FIG. 4.
Figure 4:
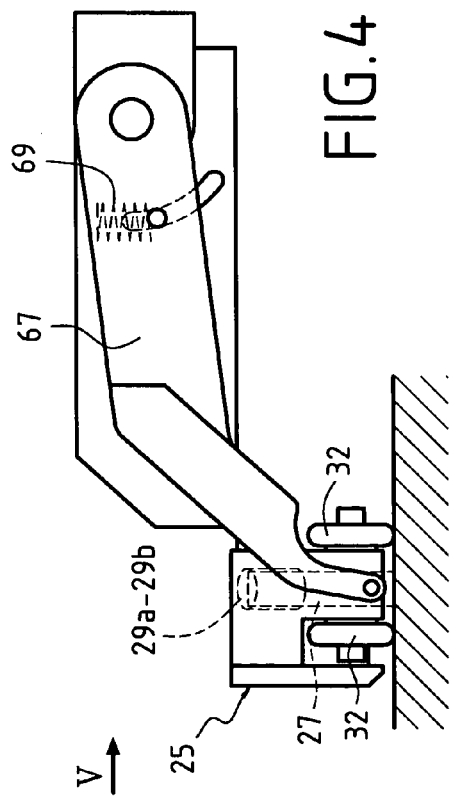
FIG. 4 is a detail view showing a sensor support.
Figure 6:
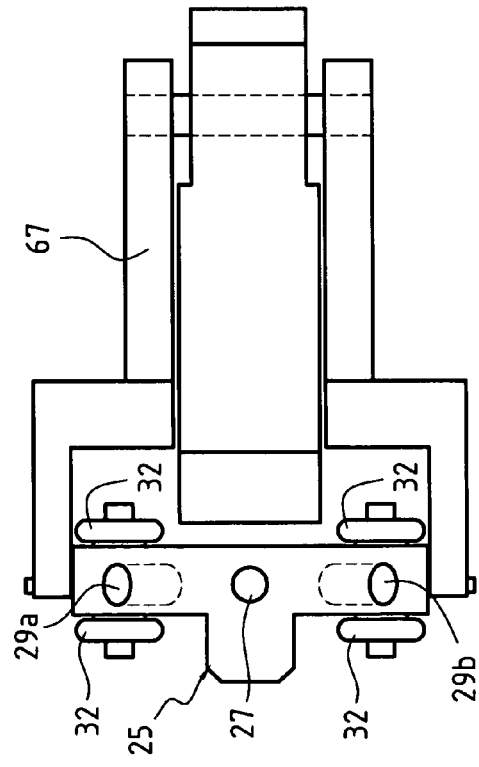
FIG. 6 is a plan view corresponding to FIG. 4.

The installation 11 for non-destructive inspection as described herein and as shown in the drawings is more specifically adapted to inspecting a part 13 forming a rotor, of the type that is to be found in an airplane turbojet, where such a wheel is also referred to as a "spool". In the jet, the part carries blades and it rotates at high speed. It is made entirely out of titanium alloy or nickel-based alloy, and it is built up from disks 15 that are welded to one another. Once it has been built, the part which is large (having a diameter of up to about 50 centimeters (cm)) is of a shape that is complex comprising a plurality of annular cavities 17 that are adjacent to one another on a common axis, being separated by annular disks 15, each presenting a thickening 19 close to its inside edge. A space 21 common to all of the cavities extends along the axis, and is thus located at the center of the part.

It is desirable specifically to inspect all of the disks 15 and more particularly to detect whether there are any inclusions therein or indeed any cracks.

In the example, provision is made to detect the inclusions mainly by ultrasound analysis and to detect cracks mainly by eddy current analysis.

Ultrasound sensors and eddy current sensors in the form of transceivers are available on the market.

More generally, the invention seeks to analyze a part using a plurality of sensors implementing different physical phenomena in order to pick up data groups specific to said sensors and corresponding respectively (for each group) to zones of the surface of each disk. The data groups are picked up by scanning said surface zone after zone. Thus, all of the necessary data is acquired in a single scan.

In this example, all of the sensors are carried on a common sensor support 25 suitable for moving over each surface to be inspected of each disk 15. The sensor support is fitted with an eddy current sensor 27 and at least one ultrasound sensor. In the example shown, the support is fitted with two ultrasound sensors 29a and 29b disposed on either side of the eddy current sensor 27. The eddy current sensor is installed on the support so as to be in register with that individual zone 31 of the surface of the disk (located perpendicularly relative thereto) that is being subjected to inspection at any given instant, while the two ultrasound sensors 29a and 29b are oriented so that their action axes converge substantially towards said individual zone. More precisely, in this configuration, the action axes of the ultrasound sensors make an angle of about 25° relative to an axis of the eddy current sensor, itself substantially perpendicular to the surface to be inspected. To ensure that the ultrasound sensors 29a, 29b do not interfere with each other, they are operated in alternation in time. The directions of these axes are selected so that the beams strike substantially the same individual zone that is being subjected to analysis by eddy currents. For example, it is possible to fire ultrasound "shots" once every 300 microseconds (μs) to 400 μs, using ultrasound beams at a frequency in the vicinity of 5 megahertz (MHz). It is also possible to offset the sensors so that they aim at zones that are adjacent but different; the essential point is that all of the data is acquired in a single scan.

As can be seen in the drawings, the sensor support 25 is in the form of a small carriage running on wheels 32 via which it contacts the surface to be inspected while it is scanning one of the disks. These simple means ensure that the sensors are always located at the desired distance from the zone under inspection. Since the disk is disposed horizontally during analysis, the carriage rests on the surface of the disk and runs thereon while data is being acquired. The wheels 32 are disposed so that their axes of rotation are oriented approximately radially relative to the disk so as to facilitate circular displacement. Scanning is performed by successive turns enabling a narrow annular band to be analyzed zone after zone. Between two turns, the carriage is caused to move through a unit radial distance in order to continue scanning on an annular band that is adjacent. The wheels may be replaced by spheres held captive in corresponding housings of the support, thus making steps in the radial direction easier to perform.

During analysis, the part 13 is rotated about its own axis of symmetry, and the support is placed on one of the disks at an adjustable radial distance. For this purpose, the installation also has a motor-driven horizontal turntable 35. The part for analysis is placed on the turntable so that its axis of symmetry coincides with the axis of rotation of said turntable. The turntable is caused to rotate at constant speed. Nevertheless, its speed is adapted to the radius of the zone being scanned so that inspection is always performed at a selected constant speed, e.g. about 300 millimeters (mm) per second.

Inspection is performed revolution after revolution with a stepwise radial displacement of about six-tenths of a millimeter between successive revolutions. It is thus possible in a single scanning operation to acquire three different "images" simultaneously of the surface of the alloy, thus making it almost certain that all of the above-mentioned faults, if any, will be detected.

Furthermore, the support is caused to move in a coupling liquid for enhancing ultrasound analysis. Specifically, this liquid is merely water. For this purpose, the turntable 35 is located in the bottom of a vessel 37 filled with water 38 so that the part 13 under analysis is completely immersed in the water throughout the inspection. Inspection, disk after disk, takes place entirely under water.

The operation begins by scanning and analyzing surfaces that extend horizontally, with changes from one surface to another being undertaken in the manner described below. Thereafter, the part 13 can be turned upside-down in order to inspect the same disks again, while scanning their other surfaces. This makes it possible reliably to detect any defects that are situated at a variety of different depths in the thickness of the metal. It should be observed that by inspecting the bottom horizontal surface within each cavity 17 it is possible to ensure that measurements are not disturbed by bubbles of air, since bubbles, if any, tend to accumulate against the top horizontal surface, i.e. the surface above the support 25, which explains why it is advantageous to turn the part upside-down in order to scan all of its surfaces.

In order to scan an annular surface of a disk using the sensor support, it is necessary to combine circular displacement with radial displacement of the support and/or the part. In the example described, it has been decided to cause the part 13 to rotate about its own axis of revolution while causing the carriage to move radially step by step. Another solution that is easy to implement consists in holding the part stationary and in causing the support 25 to move through a succession of rotations and of displacements in the radial direction. In this example, said support 25 is connected in articulated manner to the end of displacement means 41 enabling it to be moved both in rotation and radially, but given that the part itself is mounted on a turntable, the displacement means is used in this example solely for moving said carriage radially relative to the axis of rotation of the turntable.

The displacement means 41 to which the support is attached is described below. It comprises a movable vertical column 45 that is adjustable in position, installed over the turntable and arranged to engage in said space 21 that is common to said annular cavities, being defined axially at the center of the set of disks 15, together with a chain having locking links 47 mounted to slide along said column. The column is movable longitudinally along its own axis, i.e. vertically. At its bottom end it carries a deflector 49 comprising a kind of bent guide duct 51 in which said chain travels. The duct presents a lateral outlet 53 through which the chain extends substantially horizontally in the form of a rigid segment 55 in which its links are blocked mutually one against another. The end of the chain, i.e. the end of its rigid segment, is connected to at least one measurement sensor, which in the example described is the support 25 carrying the above-described set of sensors. Thus, by varying the length of the rigid segment 55, the sensor or the support 25 can be moved over the surface of one of the disks 15 in order to inspect it and detect any defects. In the example described, displacement takes place essentially radially since the part to be inspected is placed on a turntable. The axis of the column 41 coincides with the axis of rotation of the turntable 35.

In an embodiment that is described and given purely by way of example, the other end of the chain is secured to a slider 59 engaged in a kind of vertical slideway running along the column. The deflector houses a sprocket wheel 61 meshing with the chain. The sprocket wheel is driven by a controlled electric motor 63 via a system of gears. The motor may be mounted at the bottom end of the column. The chain 47 of blocking links is of known type. It is possible to use a so-called "25 pitch" chain sold under the trademark "SERAPID". Such a chain is remarkable in that its links are provided with stubs 65 that lock against one another when they are in alignment and while they are being subjected to a pivoting force in a given direction, in this case under the action of gravity. Turning the sprocket wheel 61 serves to adjust the length of the rigid horizontal segment 55 of the chain.

Controlled displacement of the column makes it possible to go from a given disk to an adjacent disk, whether below or above, while the chain is fully retracted.

The support is attached in hinged manner to the end of said rigid segment of chain via a two-arm pivoting lever 67. It is urged towards the surface to be scanned by a spring 69 so that the carriage-forming support is indeed in contact under all circumstances with the surface to be inspected.

What is claimed is:

1. An installation for non-destructive inspection of a rotor-forming part having an axis of revolution and including annular cavities axially adjacent to one another, the installation comprising a sensor support suitable for moving over a surface of said rotor-forming part to be inspected, and means for combining circular displacement and radial displacement of said support and/or of said rotor-forming part, and said support being fitted with a plurality of sensors for sensing different physical characteristics in order to pick up data groups specific to said sensors, and corresponding to respective defined zones of said surface, in a single scan thereof, wherein said rotor-forming part includes a common space extending axially between said annular cavities, the installation including a horizontal turntable on which said rotor-forming part can be placed for inspection, a vertical column movable above said turntable and arranged to engage in said common space of said rotor-forming part for inspection, a chain of locking links mounted to slide along said column, and a deflector carried by said column and comprising an angled guide duct for said chain, presenting a lateral outlet through which the chain leaves substantially horizontally in the form of a rigid segment having links blocked mutually one against another, the end of said rigid segment being connected to said sensor support to move said sensor support while facing a surface for inspection of said rotor-forming part.

2. An installation according to claim 1, wherein said sensors make use of different physical phenomena.

3. An installation according to claim 1, wherein said sensors include an eddy current sensor and at least one ultrasound sensor, and said support is fitted with said eddy current sensor and with said at least one ultrasound sensor.

4. An installation according to claim 1, wherein said sensor support includes running wheels via which said sensor support comes into contact with said surface to be inspected during said scan.

5. An installation according to claim 1, further comprising a vessel containing a coupling liquid, wherein said sensor support is constrained to move in said coupling liquid.

6. An installation according to claim 5, wherein said coupling liquid is water.

7. An installation according to claim 1, including a horizontal turntable on which said part is placed so that said axis of revolution coincides with the axis of rotation of said turntable.

8. An installation according to claim 7, wherein said turntable is installed in a vessel filled with a coupling liquid.

9. An installation according to claim 7, wherein said support is attached in hinged manner to the end of displacement means arranged to move said support radially relative to the axis of rotation of said turntable.

10. An installation according to claim 3, wherein said at least one ultrasonic sensor includes two ultrasound sensors and said support is fitted with said two ultrasound sensors disposed on either side of said eddy current sensor.

11. An installation according to claim 10, wherein said eddy current sensor is arranged to be placed facing an individual zone under inspection, and wherein the two ultrasound sensors are oriented so that action axes of said two ultrasound sensors converge substantially towards said individual zone.

12. An installation according to claim 11, wherein said action axes lie substantially in the same plane.

13. An installation according to claim 12, wherein said two ultrasound sensors are operated in alternation.

14. An installation according to claim 1, wherein said turntable is located in the bottom of a vessel shaped and dimensioned to receive said part, and wherein said vessel is filled with a coupling liquid necessary for proper operation of at least one of the said sensors.

15. An installation according to claim 1, wherein said deflector houses a sprocket wheel meshing with said chain and driven by a controlled electric motor.

16. An installation according to claim 1, wherein said deflector is connected to the bottom end of said column, and wherein said column is vertically movable to enable said deflector to be positioned at a height suitable for enabling said sensor support to scan a given annular area of said part.

17. An installation according to claim 1, wherein said turntable has a vertical axis of rotation.

* * * * *

UNITED STATES PATENT AND TRADEMARK OFFICE
CERTIFICATE OF CORRECTION

| | |
|---|---|
| PATENT NO. | : 7,305,898 B2 |
| APPLICATION NO. | : 11/143484 |
| DATED | : December 11, 2007 |
| INVENTOR(S) | : Patrick Cabanis et al. |

It is certified that error appears in the above-identified patent and that said Letters Patent is hereby corrected as shown below:

On the title page, Item (73), the Assignee information is incorrect. Item (73) should read as follows:

-- Assignee: Snecma Moteurs, Paris, (FR) --

Signed and Sealed this

Twentieth Day of May, 2008

JON W. DUDAS
*Director of the United States Patent and Trademark Office*